(12) United States Patent
Schöpp et al.

(10) Patent No.: US 11,553,970 B2
(45) Date of Patent: Jan. 17, 2023

(54) TECHNIQUE FOR TRANSFERRING A REGISTRATION OF IMAGE DATA OF A SURGICAL OBJECT FROM ONE SURGICAL NAVIGATION SYSTEM TO ANOTHER SURGICAL NAVIGATION SYSTEM

(71) Applicant: Stryker European Holdings I, LLC, Kalamazoo, MI (US)

(72) Inventors: Hans Schöpp, Freiburg (DE); Florian Herrmann, Schwanau (DE); David Hofmann, Freiburg (DE); Udo Pfrengle, Vörstetten (DE); Fabian Riegelsberger, Umkirch (DE)

(73) Assignee: Stryker European Holdings I, LLC, Kalamazoo, MI (US)

( * ) Notice: Subject to any disclaimer, the term of this patent is extended or adjusted under 35 U.S.C. 154(b) by 361 days.

(21) Appl. No.: 16/811,436

(22) Filed: Mar. 6, 2020

(65) Prior Publication Data
US 2020/0297428 A1 Sep. 24, 2020

(30) Foreign Application Priority Data
Mar. 21, 2019 (EP) .................................... 19164251

(51) Int. Cl.
*G06T 19/00* (2011.01)
*A61B 34/20* (2016.01)
(Continued)

(52) U.S. Cl.
CPC ............ *A61B 34/20* (2016.02); *A61B 5/6833* (2013.01); *A61B 90/36* (2016.02); *G06T 7/0012* (2013.01);
(Continued)

(58) Field of Classification Search
CPC ....... A61B 34/20; A61B 5/6833; A61B 90/36; A61B 2034/2051; A61B 2034/2055;
(Continued)

(56) References Cited

U.S. PATENT DOCUMENTS

| 6,235,038 B1 | 5/2001 | Hunter et al. |
| 8,457,719 B2 | 6/2013 | Moctezuma de la Barrera et al. |

(Continued)

FOREIGN PATENT DOCUMENTS

| KR | 101491922 B1 | 2/2015 |
| WO | 2016066287 A1 | 5/2016 |

OTHER PUBLICATIONS

English language abstract and machine-assisted English translation for KR 101491922 extracted from espacenet.com database on Apr. 9, 2020, 8 pages.

*Primary Examiner* — Siamak Harandi
(74) *Attorney, Agent, or Firm* — Howard & Howard Attorneys PLLC (57) ABSTRACT

A method, a controller, and a surgical hybrid navigation system for transferring a registration of three dimensional image data of a surgical object from a first to a second surgical navigation system are described. A first tracker that is detectable by a first detector of the first surgical navigation system is arranged in a fixed spatial relationship with the surgical object and a second tracker that is detectable by a second detector of the second surgical navigation system is arranged in a fixed spatial relationship with the surgical object. The method includes registering the three dimensional image data of the surgical object in a first coordinate system of the first surgical navigation system and determining a first position and orientation of the first tracker in the first coordinate system and a second position and orientation
(Continued)

of the second tracker in a second coordinate system of the second surgical navigation system.

14 Claims, 5 Drawing Sheets

(51) Int. Cl.
*A61B 90/00* (2016.01)
*G06T 7/30* (2017.01)
*G16H 30/40* (2018.01)
*A61B 5/00* (2006.01)
*G06T 7/00* (2017.01)

(52) U.S. Cl.
CPC .............. *G06T 7/30* (2017.01); *G06T 19/003* (2013.01); *G16H 30/40* (2018.01); *A61B 2034/2051* (2016.02); *A61B 2034/2055* (2016.02); *A61B 2034/2059* (2016.02); *A61B 2090/363* (2016.02); *G06T 2200/04* (2013.01); *G06T 2207/10072* (2013.01); *G06T 2207/30004* (2013.01)

(58) Field of Classification Search
CPC ...... A61B 2034/2059; A61B 2090/363; A61B 2090/0818; A61B 2090/364; A61B 2090/374; A61B 2090/3762; A61B 2090/378; A61B 2090/3945; A61B 2090/3983; A61B 2034/2063; A61B 2034/2065; G06T 7/0012; G06T 7/30; G06T 19/003; G06T 2200/04; G06T 2207/10072; G06T 2207/30004; G16H 30/40

See application file for complete search history.

(56) References Cited

U.S. PATENT DOCUMENTS

| | | | |
|---|---|---|---|
| 10,531,926 B2 | 1/2020 | Roessler | |
| 2004/0147839 A1 | 7/2004 | Moctezuma de la Barrera et al. | |
| 2006/0058604 A1 | 3/2006 | Avinash et al. | |
| 2010/0114374 A1* | 5/2010 | Cho | G06V 20/64 901/1 |
| 2011/0069867 A1* | 3/2011 | Buehner | A61B 90/39 382/294 |
| 2012/0165657 A1 | 6/2012 | Groszmann et al. | |
| 2014/0276943 A1 | 9/2014 | Bowling et al. | |

* cited by examiner

TECHNIQUE FOR TRANSFERRING A REGISTRATION OF IMAGE DATA OF A SURGICAL OBJECT FROM ONE SURGICAL NAVIGATION SYSTEM TO ANOTHER SURGICAL NAVIGATION SYSTEM

PRIORITY CLAIM

This application claims priority under 35 U.S.C. § 119 to European Patent Application No. 19164251.1, filed Mar. 21, 2019, the entire contents of which are hereby incorporated by reference.

TECHNICAL FIELD

The present disclosure generally relates to surgical navigation. In particular, a is method, a computer program product, a controller, and a system for transferring a registration of image data of a surgical object from a first surgical navigation system to a second surgical navigation system are presented.

BACKGROUND

Many surgical procedures benefit from determining positions and orientations of surgical objects, such as surgical instruments and a patient, as a basis for providing navigation instructions to a surgeon. Surgical navigation initially often requires registering three dimensional image data of a surgical object in a coordinate system (CS) of a surgical navigation system (SNS). During registration, the three dimensional image data is arranged and oriented in the CS relative to a tracker associated with the surgical object, which subsequently allows determining changes in the position and orientation of the three dimensional image data in the CS by tracking movements of the tracker.

In an exemplary application of a SNS, a surgical instrument and the patient are each associated with a tracker, wherein three dimensional image data previously obtained by, for example, a computer tomography (CT) scan is registered with the patient tracker and three dimensional image data of the surgical instrument is registered with the instrument tracker. By tracking the trackers of the patient and the surgical instrument, the SNS can determine the position and orientation of both surgical objects and calculate a spatial relationship between the three dimensional image data of the surgical instrument and of the patient. The determined spatial relationship can, for example, be displayed on a screen, helping the surgeon guide the surgical instrument relative to the patient.

During surgery, a plurality of SNSs may be used in parallel or one after the other. In such a case, the surgeon may select the SNS that best suits the task at hand. SNSs based on an optical tracking principle tend to provide high accuracy for the registration of the three dimensional image data, whereas SNSs based on an electromagnetic principle generally perform well for tracking. A surgeon provided with an optical SNS and an electromagnetic SNS can perform registration using the optical SNS and then continue tracking using the electromagnetic SNS. Consequently, surgical navigation may be improved by employing a plurality of SNSs.

In order to separate the registration and tracking steps between two SNSs, the registration performed within a first CS of a first SNS may need to be transferred to a second CS of a second SNS that is used for the tracking step afterwards. To this end, a hybrid tracker can be used that comprises a first tracker that is detectable by the first SNS and a second tracker that is detectable by the second SNS. The hybrid tracker can be attached to a surgical object such as a patient or a surgical instrument for registration with the first SNS. The position and orientation of the first tracker relative to the second tracker is known, which allows calculating a transformation for transferring the registration performed in the first CS to the second CS. Since, however, the position and orientation of the first tracker relative to the second tracker has to be known for the transformation, the surgeon cannot change the geometric properties of the hybrid tracker without having to perform additional calibration steps. The surgeon is therefore limited in his or her ability to freely select the position of both trackers.

Prior art is known from WO 2016/066287. This document discloses a system for navigating surgical instruments relative to a patient, comprising a first tracking system for measuring the position of at least one of a first type of tracker and a second tracking system for measuring the position of at least one of a second type of tracker. The system comprises at least one patient tracker belonging to the first type of tracker for measuring the position of the patient and a surgical instrument comprising a tracker belonging to the second type of tracker. The system further comprises a connector for rigidly but removably connecting the at least one of a first type of tracker with at least one of a second type of tracker for registration and/or transformation of the coordinates of the surgical instrument to the coordinates of the image data of the patient and vice versa.

SUMMARY

There is a need for a registration transfer that solves one or more of the aforementioned or other problems.

According to one aspect a method for transferring a registration of three dimensional image data of a surgical object from a first to a second surgical navigation system is provided. A first tracker that is detectable by a first detector of the first surgical navigation system is arranged in a fixed spatial relationship with the surgical object and a second tracker that is detectable by a second detector of the second surgical navigation system is arranged in a fixed spatial relationship with the surgical object. The method comprises registering the three dimensional image data of the surgical object in a first coordinate system of the first surgical navigation system and determining a first position and orientation of the first tracker in the first coordinate system and a second position and orientation of the second tracker in a second coordinate system of the second surgical navigation system. The method further comprises determining a third position and orientation of the second coordinate system in the first coordinate system and registering the three dimensional image data of the surgical object in the second coordinate system on the basis of the determined first, second and third positions and orientations.

Registering the three dimensional image data of the surgical object in the second coordinate system may comprise determining a spatial relationship of the first tracker relative to the second tracker on the basis of the determined first, second and third positions and orientations. The spatial relationship of the first tracker relative to the second tracker may be defined by a transformation.

The first tracker may be based on an optical tracking principle and the second tracker may be based on an electromagnetic tracking principle. Alternatively, both trackers may be based on the same tracking principle (e.g., electromagnetic or optical principle).

The step of determining the third position and orientation may comprise determining a position and orientation of a third tracker that is detectable by the first detector of the first surgical navigation system, wherein the third tracker is arranged in a known position and orientation in the second coordinate system. Alternatively, or in addition, this step may comprise determining a position and orientation of a fourth tracker that is detectable by the second detector of the second surgical navigation system, wherein the fourth tracker is arranged in a known position and orientation in the first coordinate system.

The third tracker may be attached to a component of the second surgical navigation system (e.g., a field generator of the second surgical navigation system). The fourth tracker may be attached to a component of the first surgical navigation system (e.g., a camera of the first surgical navigation system).

At least one of the first tracker and the second tracker may comprise a planar flexible patch that is configured to be arranged on (e.g., stuck to) a skin surface of a patient. The flexible patch may be configured to be arranged on a head surface of the patient. The planar flexible patch may comprise one or more light sources that are identifiable in the three dimensional image data and/or identifiable by the first detector. Additionally, or in the alternative, it may comprise one or more features that are identifiable in the three dimensional image data and/or identifiable by the first detector. The planar flexible patch may comprise a plurality of light sources. The features that are identifiable in the three dimensional image data may be a part of the light sources or added fiducial markers supported by the planar flexible patch.

The surgical object may comprise a patient or a surgical instrument. The surgical instrument may be configured to arrange a shunt into the patient. As such, the surgical instrument may be a shunt stylet.

The method may further comprise at least one of removing and deactivating the first tracker once the three dimensional image data of the surgical object has been registered in the second coordinate system.

Determining the first position and orientation of the first tracker in the first coordinate system and determining the second position and orientation of the second tracker in the second coordinate system may be performed at the same time. Alternatively, or in addition, this step may be performed at different points in time while the first tracker and second tracker are stationary. The determined first positions and orientations of the first tracker and the second positions and orientations of the second tracker may be stored continuously with assigned time stamps.

A fifth tracker that is detectable by the first detector of the first surgical navigation system may be arranged in a fixed spatial relationship with the surgical object. In such a case, registering the three dimensional image data of the surgical object in the first coordinate system may comprise registering the three dimensional image data of the surgical object in the first coordinate system with the fifth tracker, determining a fifth position and orientation of the fifth tracker in the first coordinate system and a sixth position and orientation of the first tracker in the first coordinate system and registering the three dimensional image data of the surgical object in the first coordinate system with the first tracker on the basis of the determined fifth and sixth position and orientation. The fifth tracker may comprise at least one fiducial marker arranged on a surface of the surgical object. The fiducial marker may also be present in the three dimensional image data to be registered. For example, the three dimensional image data may have been recorded with the fifth tracker mounted to the surgical object.

The first tracker and the second tracker may be connected in a fixed spatial relationship to each other. The first tracker and the second tracker may be connectable in such a way that after the first tracker is arranged in a fixed spatial relationship with the surgical object, the second tracker is arranged in a fixed spatial relationship with the surgical object by connecting the second tracker with the first tracker. Alternatively, the first tracker and the second tracker may be provided separately.

According to a second aspect, a computer program product is provided. The computer program product comprises instructions that, when executed on at least one processor, cause the at least one processor to carry out a method as described herein. The computer program product may be stored on a computer-readable recording medium.

According to a third aspect, a controller for transferring a registration of three dimensional image data of a surgical object from a first to a second surgical navigation system is provided. A first tracker that is detectable by a first detector of the first surgical navigation system is arranged in a fixed spatial relationship with the surgical object and a second tracker that is detectable by a second detector of the second surgical navigation system is arranged in a fixed spatial relationship with the surgical object. The controller is communicatively coupleable with the first and second surgical navigation system. The controller is configured to register the three dimensional image data of the surgical object in a first coordinate system of the first surgical navigation system. The controller is further configured to determine a first position and orientation of the first tracker in the first coordinate system and a second position and orientation of the second tracker in a second coordinate system of the second surgical navigation system. The controller is configured to determine a third position and orientation of the second coordinate system in the first coordinate system. The controller is further configured to register the three dimensional image data of the surgical object in the second coordinate system on the basis of the determined first, second and third positions and orientations.

The controller may comprise a plurality of controller devices. At least two of the controller devices may be communicatively coupled. At least a part of the method steps may be performed by different controller devices.

According to a fourth aspect, a surgical hybrid navigation system is provided. The hybrid navigation system comprises a controller as described herein, the first surgical navigation system, and the second surgical navigation system. The controller is communicatively coupled with the first and second surgical navigation system.

BRIEF DESCRIPTION OF THE DRAWINGS

Further details, advantages and aspects of the present disclosure will become apparent from the following embodiments taken in conjunction with the drawings, wherein.

DETAILED DESCRIPTION

In the following description, exemplary embodiments of a surgical hybrid navigation system, a controller, and a method for transferring a registration of a surgical object will be explained with reference to the drawings. The same reference numerals will be used to denote the same or similar structural features.

Figure 1:
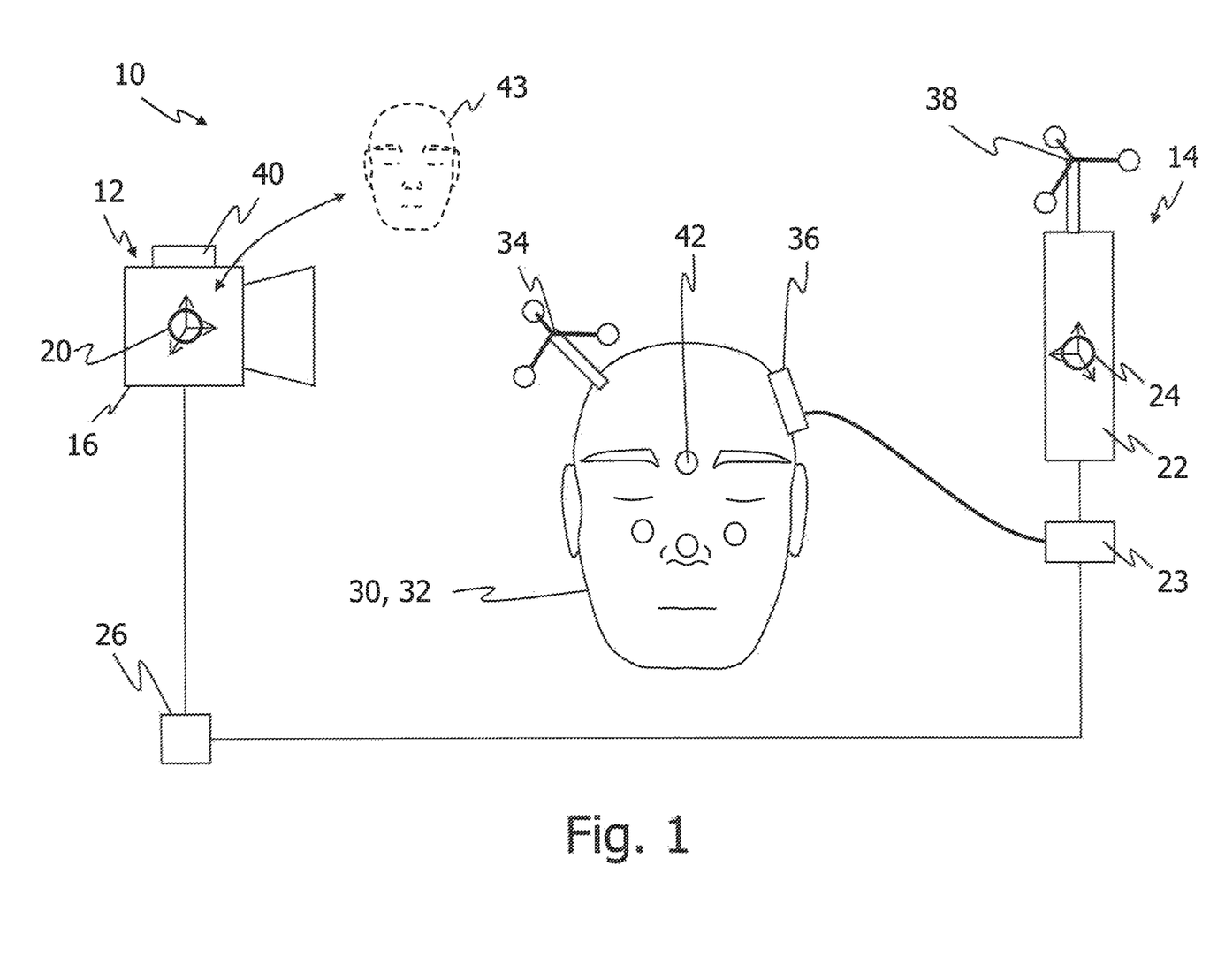
FIG. 1 shows a perspective view of an embodiment of a surgical hybrid navigation system.

FIG. 1 shows a perspective view of an embodiment of a surgical hybrid navigation system 10. The surgical hybrid navigation system 10 comprises a first surgical navigation system (SNS) 12. The first SNS 12 comprises an optical camera 16. The camera 16 is configured to detect light emitted by and/or reflected off optical trackers 34, 38. The first SNS 12 therefore allows tracking based on an optical tracking principle. The camera 16 is configured to detect at least one of infrared light, visible light, and ultraviolet light. The first SNS 12 is associated with a first coordinate system (CS) 20. The first CN 20 is, for example, arranged in a specific relationship to an image plane of the camera 16. Alternatively, the first CN 20 may be arranged in a different location with a known distance and orientation relative to a component of the camera 16 (such as the image plane or an objective of the camera 16).

The surgical hybrid navigation system 10 further comprises a second SNS 14. The second SNS 14 comprises a field generator 22 configured to create an electromagnetic field. The electromagnetic field is configured to induce currents in coils (not shown) of each of electromagnetic trackers 36, 40 exposed to the electromagnetic field. Based on the induced currents, a position and orientation of such electromagnetic trackers 36, 40 can be determined. Therefore, the second SNS 14 allows tracking based on an electromagnetic tracking principle. The second SNS 14 is associated with a second CS 24. The second CS 24 is arranged in a field generating region of the field generator 22. Alternatively, the second CN 24 may be arranged in a different location with a known position and orientation relative to a component of the field generator 22.

The surgical hybrid navigation system 10 further comprises a controller 26. The controller 26 is communicatively connected to components of the first SNS 12 and the second SNS 14. The controller 26 shown in FIG. 1 is a single controller device (e.g., a computer) that is communicatively connected to the first and second SNS 12, 14. Alternatively, the controller 26 may comprise a plurality of controller devices. The controller 26 may, for example, comprise a first and second controller device (not shown) that are communicatively connected to each other, wherein the first controller device is communicatively connected to the first SNS 12 and the second controller device is communicatively connected to the second SNS 14. Further alternatively, the controller 26 may comprise a first and second controller device (not shown) and a third controller device (not shown) that is communicatively connected to the first and second controller devices. In such a case, the third controller device may be configured to instruct the first and second controller devices to perform the method described therein, which allows retrofitting already existing SNSs.

The controller 26 is communicatively coupled directly or indirectly over the first SNS 12 with the camera 16 and is therefore configured to receive signals from the camera 16. The controller 26 may be configured to control the camera 16, such as activating/deactivating the camera 16 and causing the camera to record image data.

The controller 26 is communicatively coupled directly or indirectly over the second SNS 14 with the field generator 22 and is therefore configured to receive signals from the field generator 22. The controller 26 is configured to control the field generator 22, such as activating/deactivating the field generator 22 and causing the field generator 22 to generate an electromagnetic field.

In the center of FIG. 1 is shown a surgical object 30 in form of a patient 32. Other examples of surgical objects 30 are surgical instruments, as will be described further below. At the top portion of the head of the patient 32 are attached a first tracker 34 and a second tracker 36.

The first tracker 34 is an optical tracker. The first tracker 34 shown in FIG. 1 comprises three reflectors that are configured to reflect light detectable by the camera 16. Alternatively, the first tracker 34 may comprise light sources (e.g., light emitting diodes) that emit light that is detectable by the camera 16. The first tracker 34 may comprise any other number of reflectors such as four or five. The distance and orientation of the light sources relative to each other is known, so that based on image data of the light sources captured by the camera 16, a first position and orientation of the first tracker 34 relative to the camera 16 and, consequently, relative to the first CS 20 may be determined. The determination of the first position and orientation is performed by the controller 26.

The second tracker 36 is an electromagnetic tracker. The second tracker 36 shown in FIG. 1 comprises coils (not shown) in which currents are induced by the electromagnetic field generated by the field generator 22. The second tracker 36 is electrically connected with a receiver 23, where an induced current or a signal indicative of the induced current is received from the second tracker 36.

Alternatively, the second tracker 36 may be electrically connected with the controller 26. The second tracker 36 shown in FIG. 1 is electrically connected with the receiver 23 by wire. Alternatively, the second tracker 36 may be configured to send the signal indicative of the induced currents to the receiver 23 or the controller 26 wirelessly.

Based on the currents or the signal indicative of the induced currents, the controller 26 can determine a second position and orientation of the second tracker 36 relative to the second CS 24. The determination may alternatively be performed by the receiver 23, wherein the result is sent by the receiver 23 to the controller 26.

The surgical hybrid navigation system 10 further comprises a third tracker 38. The third tracker 38 is an optical tracker that is detectable by the camera 16 of the first SNS 12. The third tracker 38 is arranged in a fixed spatial relationship with the second SNS 14 and therefore in a fixed spatial relationship with the second CS 24. The position and orientation of the third tracker 38 in the second CS 24 is known (e.g., determined previously and stored in the controller 26). The third tracker 38 shown in FIG. 1 is attached to the field generator 22. Alternatively, the third tracker 38 may be attached to any other component of the second SNS 14 or any other fixed component in the room, as long as the position and orientation of the third tracker 38 in the second CS 24 is known or can be derived (e.g., by manually measuring the position and orientation of the third tracker 38 during installation of the surgical hybrid navigation system 10 and entering the measurements in the controller 26).

The surgical hybrid navigation system 10 further comprises a fourth tracker 40. The fourth tracker 40 is an electromagnetic tracker that is trackable by the second SNS 14. To this end, the fourth tracker 40 has coils, in which an electromagnetic field induces currents, and is configured to send the induced currents or a signal indicative of the induced currents via wire (not shown) to the controller 26. The signal indicative of the induced currents may alternatively be sent to the controller 26 wirelessly. The fourth tracker 40 is arranged in a fixed spatial relationship with the first SNS 12 and therefore in a fixed spatial relationship with the first CS 20. The position and orientation of the fourth tracker 40 in the first CS 20 is known (e.g., has been previously determined and stored in the controller 26). The fourth tracker 40 shown in FIG. 1 is attached to the camera 16. Alternatively, the fourth tracker 40 may be attached to any other component of the first SNS 12 or any other fixed component in the room, as long as the position of orientation of the fourth tracker 40 in the first CS 20 is known or can be derived (e.g., by manually measuring the position and orientation of the fourth tracker 40 during installation of the surgical hybrid navigation system 10 and entering the measurements in the controller 26).

Attached to the patient 32 is a fifth tracker 42 that comprises fiducial markers. Fiducial markers are detectable by a medical imaging device that generates three dimensional image data of the surgical object 30 (e.g., due to a material type or density of the fiducial markers). Therefore, the fiducial markers can later be identified in the three dimensional image data.

The fifth tracker 42 comprises four fiducial markers attached to a surface of the patient 32. The fifth tracker 42 may alternatively comprise any other number of fiducial markers. The fifth tracker 42 is detectable by the camera 16 of the first SNS 12. The fiducial markers shown in FIG. 1 are light weight and do not restrict the movement of the patient 32. Therefore, the fifth tracker 42 can be easily worn by the patient 32 while generating three dimensional image data 43 of the patient 32. Since the fiducial markers are identifiable in the three dimensional image data 43, they allow registration of the three dimensional image data 43 with the first SNS 12. Alternatively or additionally, the fifth tracker 42 may consist of facial features of the patient 32 (e.g., nose tip, chin, ear lobes, cheek bones, etc.).

The three dimensional image data 43 of the patient 32 may be obtained by any medical imaging device, such as CT scan, magnetic resonance imaging, positron emission tomography, ultrasonography or single-photon emission computed tomography.

The surgical hybrid navigation system 10 shown in FIG. 1 comprises two CSs 20, 24, in which five trackers 34, 36, 38, 40, 42 are arranged. Some spatial relationships between the trackers 34, 36, 38, 40, 42 and the CSs 20, 24 as well as between the trackers 34, 36, 38, 40, 42 themselves will be defined below, in order to describe the method for transferring the registration between the two SNSs 12, 14 afterwards.

Figure 2:
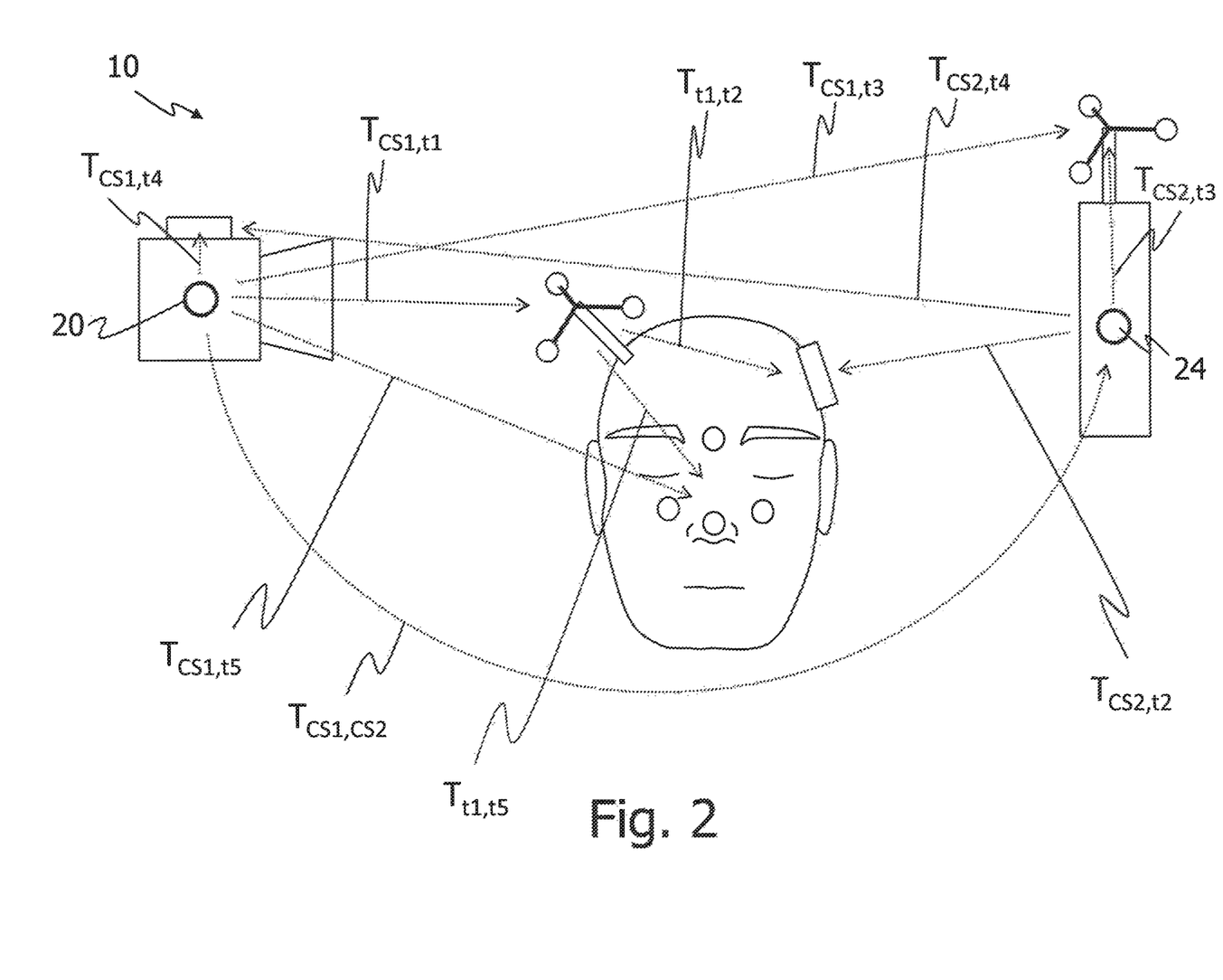
FIG. 2 shows a perspective view of transformations between components of the embodiment of the hybrid navigation system shown in FIG. 1.

The relevant spatial relationships are shown in FIG. 2. In order not to overburden the drawing in FIG. 2, reference signs introduced in FIG. 1 have been removed. The drawings of FIGS. 1 and 2 only differ in the denoted spatial relationships. For the identification of respective elements in FIG. 2, it is referred to the reference signs of FIG. 1. Mathematically, a position and orientation between two elements can be described by a transformation (e.g., a matrix). Therefore, in the following, the term transformation and the abbreviation "T" generally relates to a position and orientation between two elements. When denoting a transformation between two specific elements, the elements are indicated as an index and separated by a comma. For example, a position and orientation of the first tracker 34 in the first CS 20 can be referred to as a transformation of (the origin of) the first CS 20 to the first tracker 34, or in short "$T_{CS1,t1}$", wherein CS1 stands for the first CS 20 and t1 stands for the first tracker 34.

Consequently, FIG. 2 shows the following transformations $T_{CS1,t1}$ between the first CS 20 and first tracker 34,
$T_{CS1,t3}$ between the first CS 20 and third tracker 38,
$T_{CS1,t4}$ between the first CS 20 and fourth tracker 40,
$T_{CS1,t5}$ between the first CS 20 and fifth tracker 42,
$T_{CS1,CS2}$ between the first CS 20 and the second CS 24,
$T_{CS2,t2}$ between the second CS 24 and second tracker 36,
$T_{CS2,t3}$ between the second CS 20 and third tracker 38,
$T_{CS2,t4}$ between the second CS 24 and fourth tracker 40,
$T_{t1,t2}$ between the first tracker 34 and second tracker 36, and
$T_{t1,t5}$ between the first tracker 34 and fifth tracker 42,
wherein the index abbreviation
CS1 denotes the first CS 20,
CS2 denotes the second CS 24,
t1 denotes the first tracker 34,
t2 denotes the second tracker 36,
t3 denotes the third tracker 38,
t4 denotes the fourth tracker 40, and
t5 denotes the fifth tracker 42.

With the relevant spatial relationships defined as above, the method for transferring a registration of the surgical object 30 will be described below.

Figure 3:
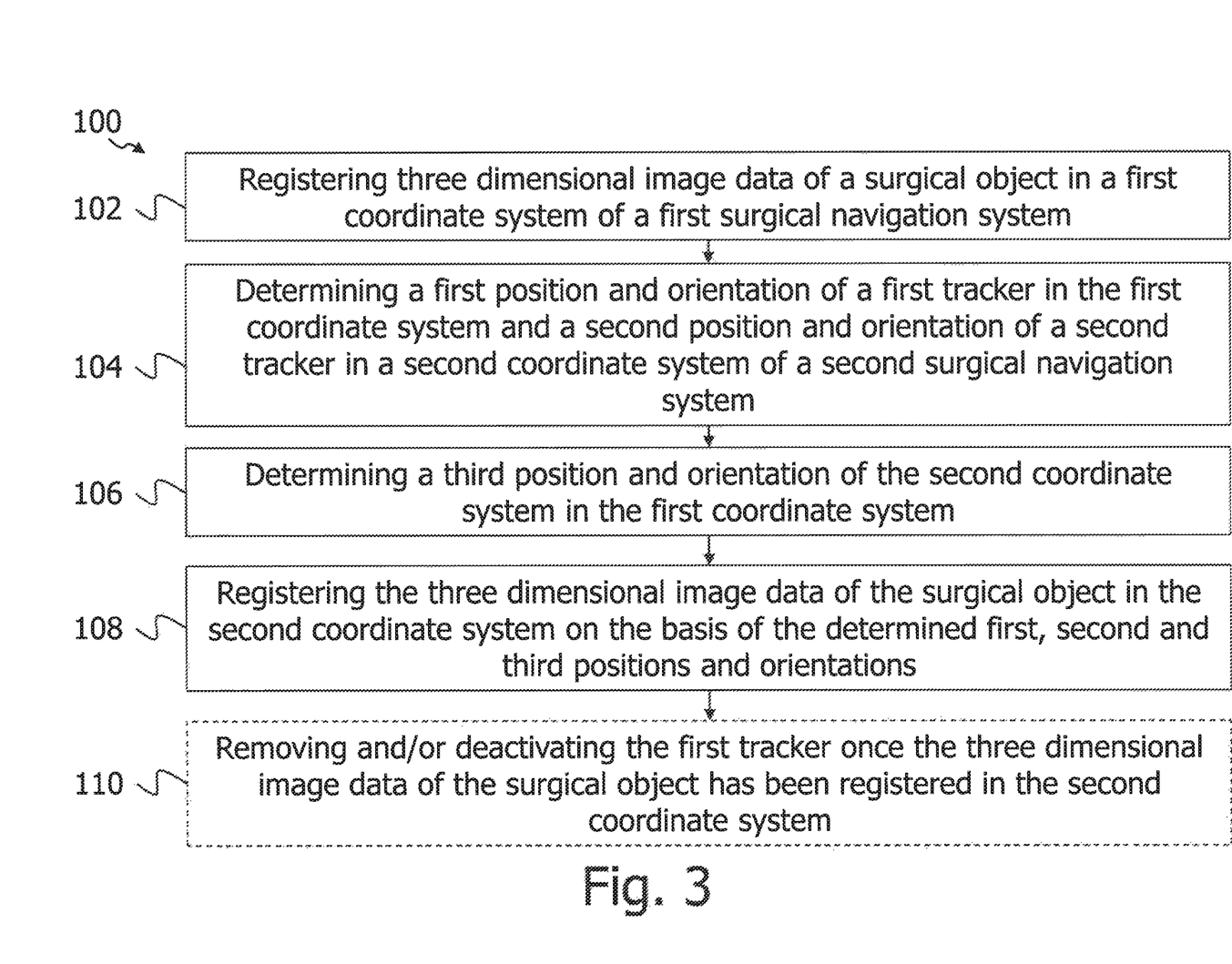
FIG. 3 shows a flow diagram of a method for transferring a registration of three dimensional image data of a surgical object from a first coordinate system of a first surgical navigation system to a second coordinate system of a second surgical navigation system.

FIG. 3 shows a flow diagram of a method 100 for transferring a registration of the surgical object 30 between a first CS 20 of a first SNS 12 and a second CS 24 of a second SNS 14.

The method comprises in step 102 registering three dimensional image data 43 of the surgical object 30 in the first CS 20 of a first SNS 12. The three dimensional image data 43 is obtained by any medical imaging device, such as CT scan, magnetic resonance imaging (MRI), positron emission tomography (PET), ultrasonography or single-photon emission computed tomography.

In order to register the three dimensional image with any tracker detectable by the first SNS 12, that tracker requires two different identifiable features: fiducial markers that are detectable by the medical imaging device (which allows identification of the tracker in the three dimensional image data), and geometrical features that are detectable by the first SNS 12, such as reflectors or light sources.

As can be seen in FIG. 1, the first tracker 34 comprises reflectors and therefore geometrical features detectable by the first SNS 12. The tracker 34 may further comprise fiducial markers detectable by the medical imaging device. Such fiducial markers may, for example, be arranged inside the reflectors.

In such a case, the three dimensional image data can be directly registered with the first tracker 34. To this end, the first tracker 34 is attached to the surgical object 30 while obtaining the three dimensional image data 43. The fiducial markers of the first tracker 34 are then identified (e.g., manually or by software) in the three dimensional image data 43. Then, the camera 16 of the first SNS 12 captures an image of the surgical object 30 and the first tracker 34 attached thereto. As explained above, the first tracker comprises geometrical features (e.g., light sources, light reflectors, geometric shapes, etc.) with known geometric properties. Due to the known geometric properties, a position and orientation of the first tracker 34 in the first CS 20 (i.e. the transformation $T_{CS1,t1}$) can be determined. The transformation $T_{CS1,t1}$ is determined by the controller 26.

For the registration of the three dimensional image data 43 in the first CS 20, a transformation is determined that aligns the fiducial markers of the first tracker 34 identified in the three dimensional image data 43 with the first tracker 34 identified in the first CS 20 by the camera 16. One way to perform the alignment is to define a tracker alignment point and a tracker alignment vector of the tracker 34 (e.g., in a geometrical center of the first tracker 34) in the first CS 20 and an image alignment point and an image alignment vector assigned to the three dimensional data. Then, the three dimensional image data 43 is translated in the first CS 20 in such a way that the tracker alignment point is aligned with the image alignment point. Furthermore, the three dimensional image data 43 is rotated in the first CS 20 in such a way that the tracker alignment vector is aligned with the image alignment vector.

The first tracker 34 shown in FIGS. 1 and 2 is an extrinsic tracker (i.e., not a part of the surgical object 30, 32), which extends away from the surgical object 30 and therefore provides a large angle of visibility. Alternatively, the first tracker 34 may be an extrinsic tracker that does not extend away from the surgical object 30 such as flat surface markers, which are more compact. Further alternatively, the first tracker 34 may be in intrinsic tracker that is defined by anatomical features of the patient 32 (e.g., nose tip, chin, ear lobes, cheek bones, etc.), which require no attachment of external trackers to the patient 32.

The registration is described above was performed directly with the first tracker 34. Alternatively, in an optional intermediate step, the three dimensional image data 43 may first be registered with a different tracker first. This may be required, for example, if the first tracker 34 does not comprise markers that are identifiable in the three dimensional image data. The three dimensional image data 43 may first be registered with the intermediate tracker (which, for example, comprises fiducial markers), whereupon the registration is then transferred to the first tracker 34. One example of such an intermediate tracker is the fifth tracker 42.

To this end, the three dimensional image data 43 is first obtained while the fifth tracker 42 is attached to the patient 32. While the three dimensional image data 43 is obtained, the patient 32 is not required to wear the first tracker 34. Afterwards, the three dimensional image data 43 is registered with the first CS 20 via the fifth tracker 42 as described above for the first tracker 34.

Next, the registration with the fifth tracker 42 is transferred to the first tracker 34. Therefore, a fifth position and orientation of the fifth tracker 42 in the first CS 20 and a sixth position and orientation of the first tracker 34 in the first CS 20 are determined. The differentiation between the first and sixth positions and orientations of the first tracker 34 only takes into account the different registration procedures described herein. In FIGS. 1 and 2, the first and sixth positions and orientations of the first tracker 34 are identical (i.e., transformation $T_{CS1,t1}$).

In order to transfer the registration of the three dimensional image data 43 from the fifth tracker 42 to the first tracker 34, the transformation $T_{t1,t5}$ between the first tracker 34 and the fifth tracker 42 is required. As can be seen in FIG. 2, the transformation $T_{t1,t5}$ is the difference between the transformations $T_{CS1,t1}$ and $T_{CS1,t5}$:

$$T_{t1,t5} = T_{CS1,t5} - T_{CS1,t1}.$$

The transformations $T_{CS1,t1}$ and $T_{CS1,t5}$ can be determined based on image data captured by the camera 16 of the first SNS 12. The three dimensional image data 43 can then be registered with the first tracker 34 based on the registration with the fifth tracker 42 and the transformation $T_{t1,t5}$. To this end, the image alignment point at which the three dimensional image data 43 is aligned with the tracker is transformed with the transformation $T_{t1,t5}$ (or more specifically— $T_{t1,t5}$) from the tracker alignment point of the fifth tracker 42 to a tracker alignment point of the first tracker 34.

The registration transfer between the first tracker 34 and the fifth tracker 42 is less complicated, as both trackers 34, 42 are tracked by the same SNS 12 and therefore in the same first CS 20. However, transferring registration between two trackers that are tracked in different CS of difference SNSs requires additional steps.

To recap, the three dimensional image data 43 has been registered in the first CS 20 with the first tracker 34. The registration may be performed directly with the first tracker 34 (e.g., because the first tracker 34 comprises fiducial markers). Optionally, the registration of the three dimensional with the first tracker 34 may comprise an intermediate step, wherein the three dimensional image data 43 is first registered with the fifth tracker 42 (e.g., because obtaining three dimensional image data 43 is easier with the fifth tracker 42). Afterwards, the registration is transferred from the fifth tracker 42 to the first tracker 34. In both cases, the three dimensional image data 43 ends up being registered with the first tracker 34. As will be described below, this registration will then be transferred to the second tracker 36 in the second CS 24.

The method 100 comprises in step 104 determining a first position and orientation of the first tracker 34 in the first CS 20 (i.e., the transformation $T_{CS1,t1}$) and a second position and orientation of a second tracker 24 in the second CS 24 (i.e., the transformation $T_{CS2,t2}$) of the second SNS 14. The transformation $T_{CS1,t1}$ is determined based on image data of the first tracker 34 captured by the camera 16. The transformation $T_{CS2,t2}$ is determined based on an induced current in the second tracker 36 or a signal indicative of the induced current in the second tracker 36 received at the receiver 23 or the controller 26.

The determination of the transformations $T_{CS1,t1}$, $T_{CS2,t2}$ is performed at the same time and while the first tracker 34 and the second tracker 36 are stationary. The transformations $T_{CS1,t1}$, $T_{CS2,t2}$ and $T_{t1,t2}$ are consequently constant. Alternatively, the determination of the transformations $T_{CS1,t1}$, $T_{CS2,t2}$ may be performed with a temporal offset (i.e., at two different points in time) while the first tracker 34 and the second tracker 36 are stationary. Since the first tracker 34 and the second tracker 36 are stationary, a temporal offset does not affect the determined transformations $T_{CS1,t1}$, $T_{CS2,t2}$. Furthermore, the determined transformations $T_{CS1,t1}$, $T_{CS2,t2}$ may be recorded continuously, wherein consecutive time slots are assigned respective determined transformations $T_{CS1,t1}$, $T_{CS2,t2}$. Such a recorded timeline of transformations provides a database for a registration transfer with the option to perform the transfer during movement of the first and second tracker 34, 36. For example, the transformations $T_{CS1,t1}$, $T_{CS2,t2}$ to be used for a registration transfer may be determined at a first point of time $t_1$, whereas the calculations for the registration transfer are completed later at a second point of time $t_2$ (e.g., due to a processing time required for the calculations). The registration transfer can then be applied to the transformations $T_{CS1,t1}$, $T_{CS2,t2}$ of the point of time $t_1$ but then updated retroactively taking into account the timeline of transformations $T_{CS1,t1}$, $T_{CS2,t2}$ that occurred between the two points in time $t_1$ and $t_2$. The recorded timeline of the transformations therefore allows a registration transfer without interrupting a movement of the first and second tracker 34, 36.

The method 100 further comprises in step 106 determining a third position and orientation (i.e., transformation $T_{CS1,CS2}$) of the second CS 24 in the first CS 20. To this end, the second SNS 14 is provided with the third tracker 38, which is detectable by the first SNS 12. The position and orientation of the third tracker 38 (i.e. transformation $T_{CS2,t3}$) relative to the second CS 24 are known and stored or manually entered in the controller 26. Furthermore, geometric properties of the third tracker 38 (e.g., spatial relationship of light sources and/or reflectors or the geometric shape of the third tracker 38) are known. Therefore, based on the image data obtained by the camera 16 of the first SNS 12, an orientation and position of the third tracker 38 in the first CS 20 (i.e., transformation $T_{C1,t3}$) can be determined.

As can be seen in FIG. 2, the transformation $T_{CS1,CS2}$ is the difference be the transformations $T_{CS1,t3}$ and $T_{CS2,t3}$:

$$T_{CS1,CS2} = T_{CS1,t3} - T_{CS2,t3}.$$

Therefore, since $T_{CS2,t3}$ is known and $T_{C1,t3}$ is determined via the first SNS 12, the transformation $T_{CS1,CS2}$ can be determined.

Alternatively, the transformation $T_{CS1,CS2}$ may be obtained by determining a position and orientation of the fourth tracker 40 (i.e., the transformation $T_{CS2,t4}$) via the second SNS 14 and a known position and orientation of the fourth tracker 40 relative to the first CS 20 (i.e., the transformation $T_{CS1,t4}$).

As can be seen in FIG. 2, the transformation $T_{CS1,CS2}$ is the difference be the transformations $T_{CS2,t4}$ and $T_{CS1,t4}$:

$$T_{CS1,CS2} = T_{CS1,t4} - T_{CS2,t4}.$$

To summarize, the transformation $T_{CS1,CS2}$ can be obtained by determining with one of the SNSs 12, 14 a position and orientation of a tracker that is arranged in a known spatial relationship in the CS 20, 24 of the other SNS 14, 12. FIGS. 1 and 2 show both trackers 38, 40 for each calculation path. However, for determining the transformation $T_{CS1,CS2}$, only one of the trackers 38, 40 is necessary. Both trackers 38, 40 may still be provided for the sake of redundancy.

In FIGS. 1 and 2, the third and fourth trackers 38, 40 are shown to be attached to components of the SNSs 14, 12. Such an attachment allows movement of these components without changing the known transformations $T_{CS2,t4}$ and $T_{CS2,t3}$. However, the third and/or fourth tracker 38, 40 may be attached do any other structure that is arranged in a detection vicinity of the SNSs 12, 14.

The method 100 then comprises in step 108 registering the three dimensional image data 43 of the surgical object 30 in the second CS 24 on the basis of the determined first, second and third positions and orientations (i.e., $T_{CS1,t1}$, $T_{CS2,t2}$ and $T_{CS1,CS2}$). In order to transfer the registration of the three dimensional image data 43 from the first tracker 34 to the second tracker 36, the position and orientation of the second tracker 36 relative to the first tracker 34 (i.e., the transformation $T_{t1,t2}$) is required. The transformation $T_{t1,t2}$ may not be known (e.g., because the surgeon freely placed the trackers 34, 36) or may be known, but is to be confirmed.

As can be seen in FIG. 2, the transformation $T_{t1,t2}$ can be calculated from a difference of the transformations $T_{CS1,CS2}$, $T_{CS2,t2}$ and $T_{CS1,t1}$:

$$T_{t1,t2} = T_{CS1,CS2} + T_{CS2,t2} - T_{CS1,t1}.$$

The transformations $T_{CS1,CS2}$, $T_{CS2,t2}$, and $T_{CS1,t1}$ have been determined in the steps described above, which allows determining $T_{t1,t2}$. The transformation $T_{t1,t2}$ is used in order to transfer the registration of the three dimensional image data 43 of the surgical object 30 from the first tracker 34 to the second tracker 36.

For the registration transfer, the transformation $T_{t1,t2}$ can be used to locate one of the two trackers 34, 36 based on a position and orientation the other one of the two trackers 36, 34. Because the transformation $T_{t1,t2}$ can be used in both CS 20 and 24, there are the two approaches. However, any approach can be used, since both approaches are equivalent.

In the first approach, the transformation $T_{t1,t2}$ is applied to the position and orientation of the first tracker 34 in the first CS 20, which results in the position and orientation of the second tracker 36 in the first CS 20. With the positions and orientations of the second tracker 36 and the three dimensional image data 43 in the first CS 20 now known, a spatial relationship between the second tracker 36 and the three dimensional image data 43 can be determined. This spatial relationship is identical in the second CS 24. Therefore, by transferring the three dimensional image data 43 with this spatial relationship to the known position and orientation of the second tracker 36 in the second CS 24, the three dimensional image data 43 is registered in the second CS 24.

In the second approach, transformation $T_{t1,t2}$ (or more specifically—$T_{t1,t2}$) is applied to the second tracker 36 in the second CS 24, which results in the position and orientation of the first tracker 34 in the second CS 24. Since the three dimensional image data 43 is registered in the first CS 20, a spatial relationship between the first tracker 34 and the three dimensional image data 43 is known. This spatial relationship is identical in the second CS 24. Therefore, by transferring the three dimensional image data 43 with this spatial relationship to the position and orientation of the first tracker 34 determined (via the transformation $T_{t1,t2}$) in the second CS 24, the three dimensional image data 43 is registered in the second CS 24.

As a result, the registration is transferred to the second tracker 36, which can now be used to track the surgical object 30.

The method 100 may optionally comprise in step 110 removing and/or deactivating the first tracker 34 once the three dimensional image data 43 of the surgical object 30 has been registered in the second CS 24. Since the surgical object 30 may now be tracked via the second SNS 14 only, the tracking process via the first SNS 12 can be cancelled. To this end, the first tracker 34 and/or the first SNS 12 may be deactivated in order to reduce power consumption. Additionally or alternatively, the first tracker 34 may be removed from the surgical object 30, which reduces possible obstructions caused by the first tracker 34 at the site of surgery. Alternatively, operation of the first SNS 12 and the first tracker 34 may be continued in order to provide redundancy or in order to switch back the registration of the three dimensional image data 43 to the first tracker 34 at a later point of time.

Figure 4:
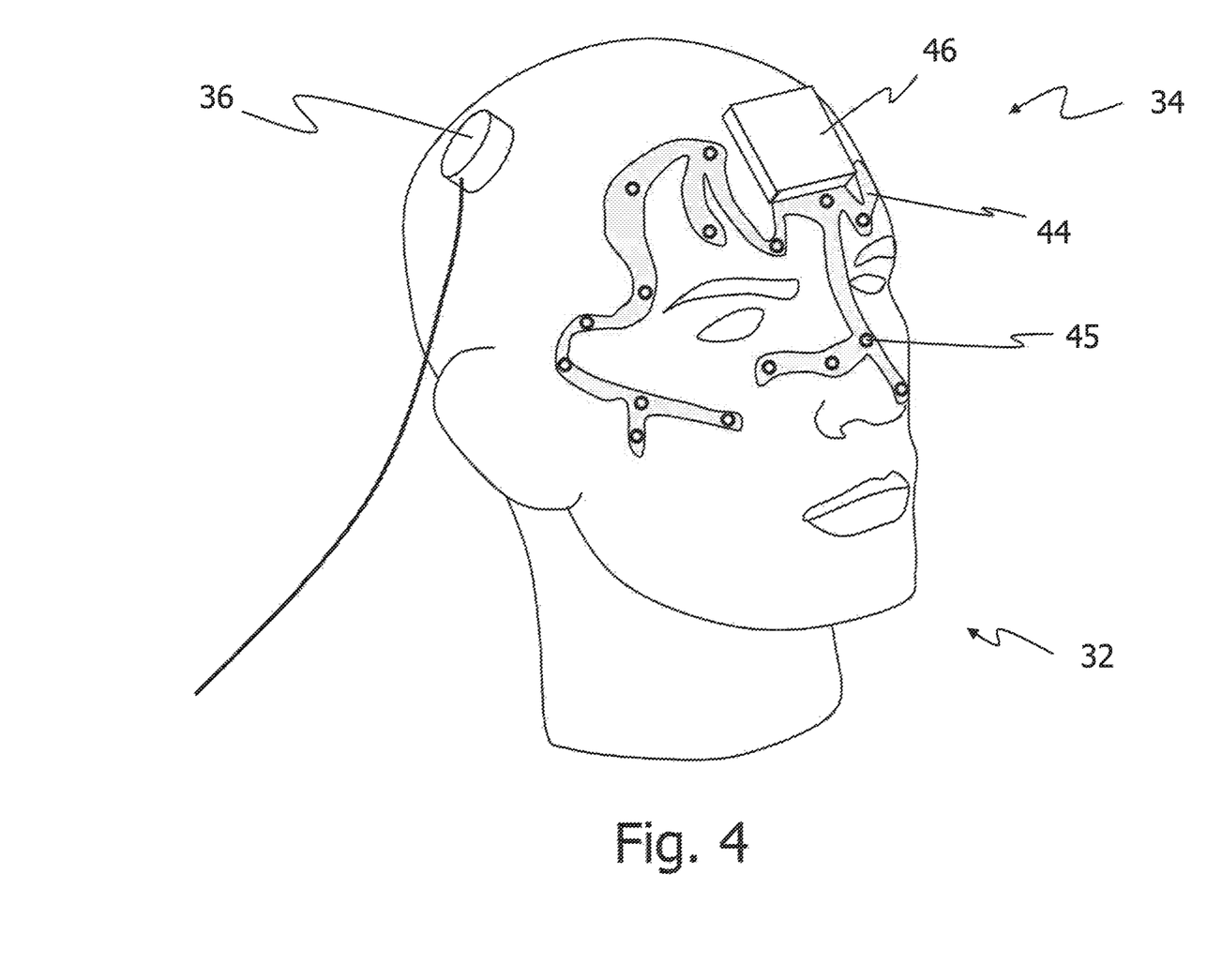
FIG. 4 shows an example of a first tracker that comprises a planar flexible patch that is configured to be arranged on a skin surface of a patient.

FIGS. 1 and 2 show the first tracker 34 in form of an extrinsic tracker with reflectors extending away from the surface of the surgical object 30. As already explained above, the first tracker 34 may alternatively comprise flat surface markers or consist of intrinsic features (e.g., nose tip). FIG. 4 shows another example of a first tracker 34 that comprises a planar flexible patch 44 that is configured to be stuck on a skin surface of the patient 32. The patch 44 comprises a plurality of light sources 45 (such as light emitting diodes) and wiring (not shown) that connects the light sources 45 with a tracker controller 46. Alternatively, the patch 44 may not comprise any light sources 45 and is tracked by the first SNS 12 due to the shape of the patch 44 or a geometric pattern on the patch 44. The tracker controller 46 comprises a power supply such as a battery or a power interface (e.g., a wiring or a wireless power transfer) to a power supply separate from the first tracker 34. The patch 44 has a flat shape resulting in a compact tracker geometry that can be easily worn in a confined space such as a CT scanner for capturing the three dimensional image data 43. Unlike flat surface markers, the patch 44 is configured to emit light, which allows accurate tracking by the first SNS 12.

For a registration of the three dimensional image data 43 with the flexible patch 44, two different approaches are possible depending on whether or not the patient 32 wears the flexible patch 44 while the three dimensional image data 43 is obtained.

In the case that the patient 32 does not wear the flexible patch 44 while the three dimensional image data 43 is obtained, a surface of the patient 32 is determined in the obtained three dimensional image data 43. Determining the surface may be performed manually or by software (e.g., based on density gradients in the three dimensional image data 43). Then, the flexible patch 44 is attached to the surface of the patient 32 and the camera 16 generates image data of the flexible patch 44, whereupon the flexible patch 44 is identified in the image data on the basis of the light sources 45 or other geometrical features. Afterwards, the surface of the patient 32 determined in the three dimensional image data 43 is aligned with the flexible patch 44 identified in the first CS 20 based on the image data of the camera 16.

In the case that the patient 32 does wear the flexible patch 44 while the three dimensional image data is obtained, features of the flexible patch 44 are determined in the obtained three dimensional image data 43. The determined features may be electrical parts (e.g., the light sources 45, or parts of its wiring) and/or added fiducial markers (not shown) supported by the flexible patch 44. Then, the camera 16 generates image data of the flexible patch 44, whereupon the flexible patch 44 is identified in the first CS 20 based the light sources 45 or other geometrical features identified in the image data. Afterwards the features of the flexible patch 44 determined in the three dimensional image data 43 are aligned with features of the flexible patch 44 identified in the image data.

Once the three dimensional image data 43 is registered with the flexible patch 44 of the first tracker 34, the registration can be transferred to the second tracker 36 as described above. To this end, the first position and orientation of the first tracker 34 and the second position and orientation of the second tracker 36 are determined. The third position and orientation of the second CS 24 in the first CS 20 is determined based on the position and orientation determined for the third tracker 38. Based on the first, second, and third positions and orientations, the three dimensional image data of the patient 32 is registered in the second CS 24 (e.g., via the transformation $T_{t1,t2}$).

Since the method described herein allows determining the transformation $T_{t1,t2}$ independent from the spatial relationship between the first and second trackers 34, 36, the surgeon can arrange the second tracker 36 freely relative to the first tracker 34. As shown in FIG. 4, the first tracker 34 and the second tracker 36 are arranged separately and therefore independently from each other. This allows the surgeon to position the second tracker 36 in such a way that the second tracker 36 does not obstruct the surgery site.

However, it is not required to arrange the first and second tracker 34, 36 separate from each other. The first and second tracker 34, 36 may also be arranged in a known predefined spatial relationship relative to each other. The method described herein may then, for example, be used in order to confirm the predefined spatial relationship between the first and second trackers 34, 36. The controller 26 may be configured to determine if a difference between the predetermined spatial relationship and the transformation $T_{t1,t2}$ determined by the method described herein exceeds a predetermined threshold. In case the predetermined threshold is exceeded, a warning may be output by the controller 26. Additionally or alternatively, the controller 26 may be configured to perform a calibration or output instructions for a recalibration of the predetermined spatial relationship.

The predetermined spatial relationship between the first tracker 34 and the second tracker 36 may be realized by a fixed connection between the first and second trackers 34, 36. The fixed connection can be provided by a rigid connector (not shown). The first and second trackers 34, 36 may be fixedly attached to the connector. Alternatively, at least one of the first tracker 34 and the second tracker 36 may be releasably attached to the connector.

For example, in FIG. 4, the second tracker 36 may instead be fixedly or releasably attached to a component of the first tracker 34, such as the tracker controller 46 or the planar flexible patch 44.

The surgical object 30 shown in FIGS. 1 to 3 is a patient 32. Alternatively, the surgical object 30 may be a surgical instrument. The surgical instrument may be a biopsy needle, a drill, a saw, a pointer, a cutter, a microscope or a measurement device. The surgical instrument may be an instrument configured for use in surgeries related to ear, nose and throat (ENT). The surgical instrument may be an instrument configured for use in neurosurgery (e.g., cranial surgery). The surgical instrument may be an instrument that can be moved manually or an instrument that is moved by a machine (such as a C-arm).

Figure 5:
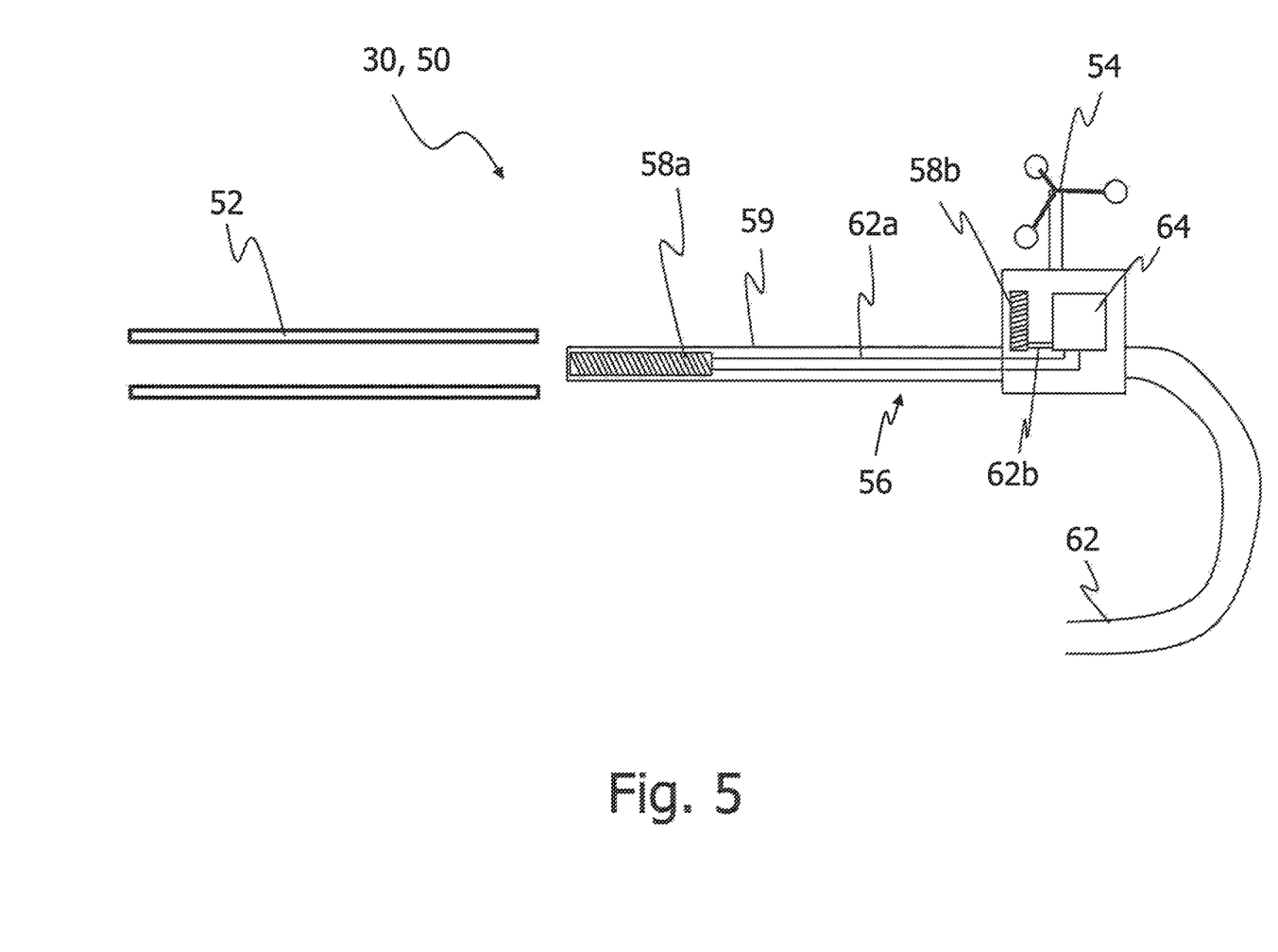
FIG. 5 shows a surgical instrument that is configured to arrange a shunt into a patient.

FIG. 5 shows an exemplary surgical instrument 50 that is configured to arrange a shunt 52 into a patient (not shown), a so-called shunt stylet. A first tracker 54 is fixedly or removably attached to the surgical instrument 50, wherein the first tracker 54 is detectable by the first SNS 12 (see FIG. 1). The first tracker 54 shown in FIG. 5 comprises light sources. Alternatively, the first tracker 54 may comprise any other feature that allows determination of its position and orientation (e.g., reflectors and/or a geometrical shape).

The surgical instrument 50 further comprises a second tracker 56 comprising two coils 58a, 58b. The coil 58a is integrated in a stylet rod 59 over which the shunt 52 can be pulled. In the surgical instrument 50 shown in FIG. 5, the second tracker 56 is a part of the surgical instrument 50. Alternatively, the second tracker 56 may be a separate component not comprised by the surgical instrument 50 that is configured to be attached to the surgical instrument 50.

The coils 58a, 58b are configured to generate currents or signals indicative of the current induced by an electromagnetic field generated by the field generator 22 of the second SNS 14 (see FIG. 1). The current or signal is sent via rod wirings 62a, 62b to an electrical interface 64. The electrical interface 64 sends the currents or signals via a tracker cable 62 to the controller 26 or the receiver 23 (see FIG. 1). Alternatively, the electrical interface 64 comprises a transmitter (not shown) that is configured to send the signals wirelessly to the controller 26. To this end, the surgical instrument 50 may comprise a battery (e.g., comprised by the electrical interface 64).

When pulled over the stylet rod 59 and the coil 58a integrated therein, the shunt 52 is mechanically connected with the surgical instrument 50 and therefore trackable by at least one of the first and second tracker 54, 56.

Three dimensional image data of the surgical instrument 50 may be provided in form of an abstract instrument axis, a technical three dimensional model or a data set generated by an external scanning procedure. The three dimensional image data is first registered in the first CS 20 of the first SNS 12 (see FIG. 1) as described above. Afterwards, the registration of the three dimensional image data is transferred into the second CS 24 of the second SNS 14 as described above.

It is noted that any of the first and second trackers 34, 36, 54, 56 may be arranged permanently in a fixed spatial relationship with a surgical object 30. This particularly applies to surgical instruments that may have a fixed attachment interface or to surgical instruments, in which the first and/or second tracker 54, 56 is integrated. The surgical instrument 50 shown in FIG. 5 is such a surgical object 30, since the second tracker 56 is partly integrated in the surgical stylet rod 59 with a fixed spatial relationship. This spatial relationship can be stored in the controller 26. The position and orientation of the surgical instrument 50 (or a component thereof, e.g., the stylus rod 59 and/or the shunt 52) can then be determined based on a position and orientation determined for the second tracker 56 and the spatial relationship between the second tracker 56 and the surgical instrument 50 stored in the controller 26. A registration with the first tracker 54 and a consecutive transfer of the registration to the second tracker 56 is then not required, but may still be performed in order to confirm the stored spatial relationship between the second tracker 56 and the surgical instrument 50 stored in the controller 26.

The registration of the three dimensional image data described herein is transferred from the first CS 20 of the first SNS 12 to the second CS 24 of the second SNS 14. One advantage of this transfer order is that optical SNSs generally provide accurate registration, whereas electromagnetic SNSs tend to provide accurate tracking without suffering from line-of-sight problems of optical SNSs. However, the approach described herein may be similarly used in order to transfer the registration from the second CS 24 to the first CS 20. The technique described herein is also not limited to optical and electrical tracking principles and can be performed to transfer a registration from SNSs that use any technical tracking principle. The method is also not limited to a single transfer but may be performed for any number of times between any number of SNSs with separate CSs.

As becomes apparent from the description of the embodiments above, the registration of three dimensional image data may be transferred between two SNSs with separate CSs, by determining a position and orientation of one CS relative to the other CS. To this end, a third and/or fourth tracker 38, 40 with a known spatial relationship with the CSs is provided. The registration transfer does not require knowledge of the orientation of the first tracker 34, 54 relative to the second tracker 36, 56, which allows arranging both trackers freely or confirming a predetermined position and orientation of both trackers relative to each other.

The features described in relation to the exemplary embodiments shown in the drawings can be readily combined to result in different embodiments. It is apparent, therefore, that the present disclosure may be varied in many ways. Such variations are not to be regarded as a departure from the scope of the invention as defined by the claims appended hereto.

The invention claimed is:

1. A method for transferring a registration of three dimensional image data of a surgical object from a first to a second surgical navigation system, wherein a first tracker that is detectable by a first detector of the first surgical navigation system is arranged in a fixed spatial relationship with the surgical object and a second tracker that is detectable by a second detector of the second surgical navigation system is arranged in a fixed spatial relationship with the surgical object, the method comprising:

registering the three dimensional image data of the surgical object in a first coordinate system of the first surgical navigation system;

determining a first position and orientation of the first tracker in the first coordinate system and a second position and orientation of the second tracker in a second coordinate system of the second surgical navigation system;

determining a third position and orientation of the second coordinate system in the first coordinate system; and registering the three dimensional image data of the surgical object in the second coordinate system on the basis of the determined first, second and third positions and orientations, wherein registering the three dimensional image data of the surgical object in the second coordinate system comprises determining a spatial relationship of the first tracker relative to the second tracker on the basis of the determined first, second and third positions and orientation.

2. The method according to claim 1, wherein the first tracker is based on an optical tracking principle and the second tracker is based on an electromagnetic tracking principle.

3. The method according to claim 1, wherein determining the third position and orientation comprises at least one of:

determining a position and orientation of a third tracker that is detectable by the first detector of the first surgical navigation system, wherein the third tracker is arranged in a known position and orientation in the second coordinate system; and determining a position and orientation of a fourth tracker that is detectable by the second detector of the second surgical navigation system, wherein the fourth tracker is arranged in a known position and orientation in the first coordinate system.

4. The method according to claim 1, wherein at least one of the first tracker and the second tracker comprises a planar flexible patch that is configured to be arranged on a skin surface of a patient.

5. The method according to claim 4, wherein the planar flexible patch comprises one or more light sources and/or one or more features that are identifiable in the three dimensional image data and/or identifiable by the first detector.

6. The method according to claim 1, wherein the surgical object comprises a patient or a surgical instrument.

7. The method according to claim 1, further comprising at least one of removing and deactivating the first tracker once the three dimensional image data of the surgical object has been registered in the second coordinate system.

8. The method according to claim 1, wherein determining the first position and orientation of the first tracker in the first coordinate system and determining the second position and orientation of the second tracker in the second coordinate system is performed at the same time or at different points in time while the first tracker and second tracker am stationary.

9. The method according to claim 1, wherein
a fifth tracker that is detectable by the first detector of the first surgical navigation system is arranged in a fixed spatial relationship with the surgical object, and wherein registering the three dimensional image data of the surgical object in the first coordinate system comprises:
 registering the three dimensional image data of the surgical object in the first coordinate system with the fifth tracker;
 determining a fifth position and orientation of the fifth tracker in the first coordinate system and a sixth position and orientation of the first tracker in the first coordinate system; and
 registering the three dimensional image data of the surgical object in the first coordinate system with the first tracker on the basis of the determined fifth and sixth positions and orientations.

10. The method according to claim 1, wherein the first tracker and the second tracker am connected in a fixed spatial relationship to each other.

11. The method according to claim 1, wherein the first tracker and the second tracker are connectable in such a way that after the first tracker is arranged in a fixed spatial relationship with the surgical object, the second tracker is arranged in a fixed spatial relationship with the surgical object by connecting the second tracker with the rut tracker.

12. A computer program product comprising a non-transitory computer-readable medium storing instructions that, when executed on at least one processor, cause the at least one processor to carry out the method of claim 1.

13. A controller for transferring a registration of three dimensional image data of a surgical object from a first to a second surgical navigation system, wherein a first tracker that is detectable by a first detector of the first surgical navigation system is arranged in a fixed spatial relationship with the surgical object and a second tracker that is detectable by a second detector of a second surgical navigation system is arranged in a fixed spatial relationship with the surgical object, wherein the controller is communicatively coupleable with the rust and second surgical navigation system and configured to:
 register the three dimensional image data of the surgical object in a first coordinate system of the first surgical navigation system;
 determine a first position and orientation of the first tracker in the first coordinate system and a second position and orientation of the second tracker in a second coordinate system of the second surgical navigation system;
 determine a third position and orientation of the second coordinate system in the first coordinate system; and
 register the three dimensional image data of the surgical object in the second coordinate system on the basis of the determined first, second and third position and orientation,
 wherein the controller is configured to register the three dimensional image data of the surgical object in the second coordinate system by being configured to determine a spatial relationship of the firm tracker relative to the second tracker on the basis of the determined first, second and third positions and orientations.

14. A surgical hybrid navigation system comprising:
the controller according to claim 13;
the rust surgical navigation system; and
the second surgical navigation system,
wherein the controller is communicatively coupled with the first and second surgical navigation system.

\* \* \* \* \*

UNITED STATES PATENT AND TRADEMARK OFFICE
CERTIFICATE OF CORRECTION

PATENT NO. : 11,553,970 B2  
APPLICATION NO. : 16/811436  
DATED : January 17, 2023  
INVENTOR(S) : Hans Schoepp et al.

Page 1 of 1

It is certified that error appears in the above-identified patent and that said Letters Patent is hereby corrected as shown below:

In the Claims

Column 17, Line 25 "and the second tracker am connected" should read "and the second tracker are connected"

Column 17, Line 32 "Connecting the second tracker with the rut tracker" should read "connecting the second tracker with the first tracker"

Column 18, Line 8 "Coupleable with the rust and second surgical navigation system" should read "coupleable with the first and second surgical navigation system"

Column 18, Line 28 "a spatial relationship of the firm tracker" should read "a spatial relationship of the first tracker"

Column 18, Line 33 "the rust surgical navigation system" should read "the first surgical navigation system"

Signed and Sealed this  
First Day of August, 2023

Katherine Kelly Vidal  
*Director of the United States Patent and Trademark Office*